United States Patent
Kawayoke

(10) Patent No.: US 10,750,940 B2
(45) Date of Patent: Aug. 25, 2020

(54) IMAGE PICKUP APPARATUS INCLUDING SOLID-STATE IMAGE PICKUP DEVICE AND ELECTRONIC COMPONENT MOUNTED ON FOLDED FLEXIBLE SUBSTRATE AND ENDOSCOPE INCLUDING THE IMAGE PICKUP APPARATUS

(71) Applicant: OLYMPUS CORPORATION, Tokyo (JP)

(72) Inventor: Shoichiro Kawayoke, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 401 days.

(21) Appl. No.: 15/812,184

(22) Filed: Nov. 14, 2017

(65) Prior Publication Data

US 2018/0070805 A1 Mar. 15, 2018

Related U.S. Application Data

(63) Continuation of application No. PCT/JP2015/065200, filed on May 27, 2015.

(51) Int. Cl.
*A61B 1/05* (2006.01)
*H01L 27/14* (2006.01)
(Continued)

(52) U.S. Cl.
CPC .......... *A61B 1/05* (2013.01); *A61B 1/00163* (2013.01); *G02B 23/2407* (2013.01);
(Continued)

(58) Field of Classification Search
CPC combination set(s) only.
See application file for complete search history.

(56) References Cited

U.S. PATENT DOCUMENTS 8,409,077 B2 * 4/2013 Orihara .............. A61B 1/00032
600/109
2003/0080434 A1 * 5/2003 Wataya ............. H01L 27/14618
257/774
(Continued)

FOREIGN PATENT DOCUMENTS

JP        H04197334 A    7/1992
JP        H05115436 A    5/1993
(Continued)

OTHER PUBLICATIONS

International Search Report dated Aug. 11, 2015 issued in PCT/JP2015/065200.

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An image pickup apparatus includes a flexible substrate, the flexible substrate includes a plurality of functional regions segmented by bending portions, one of the functional regions is an image pickup device mounting region, one of the functional regions is at least two electronic component mounting regions folded at the bending portions, and one of the functional regions is at least one wiring region provided between the adjacent mounting regions of the flexible substrate, the image pickup device mounting region has a largest surface shape among the plurality of functional regions, and the plurality of functional regions decrease in length of each of at least paired opposing sides of each surface shape, in a stepwise manner as a distance from the image pickup device mounting region increases.

12 Claims, 11 Drawing Sheets

(51) Int. Cl.
  *H04N 5/225* (2006.01)
  *H01L 27/146* (2006.01)
  *G02B 23/24* (2006.01)
  *H04N 5/335* (2011.01)
  *A61B 1/00* (2006.01)

(52) U.S. Cl.
  CPC ..... *G02B 23/2423* (2013.01); *G02B 23/2484* (2013.01); *H01L 27/14* (2013.01); *H01L 27/14601* (2013.01); *H01L 27/14634* (2013.01); *H04N 5/225* (2013.01); *H04N 5/2253* (2013.01); *H04N 5/335* (2013.01); *A61B 1/00112* (2013.01); *H04N 2005/2255* (2013.01)

(56) References Cited

U.S. PATENT DOCUMENTS

| | | | | |
|---|---|---|---|---|
| 2004/0027459 | A1* | 2/2004 | Segawa | A61B 1/0011 348/207.99 |
| 2004/0171914 | A1* | 9/2004 | Avni | A61B 1/041 600/160 |
| 2004/0225190 | A1* | 11/2004 | Kimoto | A61B 1/041 600/177 |
| 2005/0049461 | A1* | 3/2005 | Honda | A61B 1/041 600/160 |
| 2006/0264704 | A1* | 11/2006 | Fujimori | H05K 1/189 600/101 |
| 2007/0122146 | A1* | 5/2007 | Ryu | H04N 5/2253 396/529 |
| 2007/0241273 | A1* | 10/2007 | Kim | H01L 27/14625 250/239 |
| 2008/0058601 | A1* | 3/2008 | Fujimori | A61B 1/041 600/167 |
| 2008/0117324 | A1* | 5/2008 | Minamio | H04N 5/2253 348/340 |
| 2009/0268019 | A1* | 10/2009 | Ishii | A61B 1/00124 348/65 |
| 2010/0201794 | A1* | 8/2010 | Kido | A61B 1/00124 348/65 |
| 2014/0180040 | A1* | 6/2014 | Fujimori | A61B 1/00016 600/302 |
| 2015/0342530 | A1* | 12/2015 | Dekker | A61B 5/6852 600/478 |

FOREIGN PATENT DOCUMENTS

| | | |
|---|---|---|
| JP | 2008237732 A | 10/2008 |
| JP | 2009082503 A | 4/2009 |
| JP | 2009123884 A | 6/2009 |
| JP | 2010057749 A | 3/2010 |
| JP | 2012050756 A | 3/2012 |
| JP | 2013219511 A | 10/2013 |
| WO | 2009063709 A1 | 5/2009 |

* cited by examiner

IMAGE PICKUP APPARATUS INCLUDING SOLID-STATE IMAGE PICKUP DEVICE AND ELECTRONIC COMPONENT MOUNTED ON FOLDED FLEXIBLE SUBSTRATE AND ENDOSCOPE INCLUDING THE IMAGE PICKUP APPARATUS

CROSS REFERENCE TO RELATED APPLICATION

This application is a continuation application of PCT/JP2015/065200 filed on May 27, 2015, the entire contents of which are incorporated herein by this reference.

BACKGROUND OF INVENTION

1. Field of the Invention

The present invention relates to an image pickup apparatus in which a solid-state image pickup device and electronic components are mounted on a flexible substrate, and to an endoscope including the image pickup apparatus.

2. Description of the Related Art

In recent years, an image pickup apparatus in which a solid-state image pickup device and electronic components are mounted on a substrate has been used as image pickup means of a video camera, an electronic still camera, and an electronic endoscope (hereinafter, abbreviated to endoscope).

An endoscope used in a medical field includes an illumination optical system and an observation optical system that are provided at a distal end portion of an insertion section. The observation optical system includes the image pickup apparatus. The distal end portion of the insertion section is desired to have a small outer diameter in order to alleviate pain of a patient.

For example, Japanese Patent Application Laid-Open Publication No. H5-115436 discloses a solid-state image pickup apparatus that enlarges a mounting surface shape of a flexible substrate without increasing an outer shape size, thereby achieving high density and downsizing.

The above-described solid-state image pickup apparatus includes a flexible substrate that has a cross shape in an unfolded state. The flexible substrate includes an IC and a passive component on a rear surface of each of four rectangular substrate portions projected from a base portion. The IC and the passive component configure a peripheral circuit of a solid-state image pickup device. The four rectangular substrate portions are so folded along bending parts of the base portion as to face one another, which forms a cylindrical shape.

SUMMARY OF THE INVENTION

An image pickup apparatus according to an aspect of the present invention includes: one solid-state image pickup device; a plurality of electronic components; at least one signal cable; and a flexible substrate that includes a first surface and a second surface that is an opposite surface of the first surface, has predetermined flexibility, and is formed in a predetermined shape in an unfolded state, in which the flexible substrate includes a plurality of functional regions that are segmented by bending portions, one of the functional regions is one image pickup device mounting region on which the solid-state image pickup device is mounted, the image pickup device mounting region having a predetermined rectangular surface shape, one of the functional regions is at least two electronic component mounting regions on which any of the electronic components is mounted, the electronic component mounting regions being folded at the bending portions to be disposed in parallel to the image pickup device mounting region, and being fitted within a projected area of the image pickup device mounting region, one of the functional regions is at least one wiring region provided between the mounting regions adjacent to each other of the flexible substrate, the wiring region including a wiring that electrically connects at least the electronic components of the adjacent mounting regions, the wiring region being folded to cause the electronic component mounting regions to be parallel to the image pickup device mounting region, and being fitted within the projected area of the image pickup device mounting region, with the electronic component mounting regions, and the image pickup device mounting region has a largest surface shape among the plurality of stacked functional regions, and the plurality of stacked functional regions decrease in length of each of at least paired opposing sides of each surface shape, in a stepwise manner as a distance from the image pickup device mounting region increases.

An endoscope according to an aspect of the present invention includes an image pickup apparatus in a distal end portion of an insertion section that is inserted into a living body, the image pickup apparatus includes: one solid-state image pickup device; a plurality of electronic components; at least one signal cable; and a flexible substrate that includes a first surface and a second surface that is an opposite surface of the first surface, has predetermined flexibility, and is formed in a predetermined shape in an unfolded state, in which the flexible substrate includes a plurality of functional regions that are segmented by bending portions, one of the functional regions is one image pickup device mounting region on which the solid-state image pickup device is mounted, the image pickup device mounting region having a predetermined rectangular surface shape, one of the functional regions is at least two electronic component mounting regions on which any of the electronic components is mounted, the electronic component mounting regions being folded at the bending portions to be disposed in parallel to the image pickup device mounting region, and being fitted within a projected area of the image pickup device mounting region, one of the functional regions is at least one wiring region provided between the mounting regions adjacent to each other of the flexible substrate, the wiring region including a wiring that electrically connects at least the electronic components of the adjacent mounting regions, the wiring region being folded to cause the electronic component mounting regions to be parallel to the image pickup device mounting region, and being fitted within the projected area of the image pickup device mounting region, with the electronic component mounting regions, and the image pickup device mounting region has a largest surface shape among the plurality of stacked functional regions, and the plurality of stacked functional regions decrease in length of each of at least paired opposing sides of each surface shape, in a stepwise manner as a distance from the image pickup device mounting region increases.

DETAILED DESCRIPTION OF THE PREFERRED EMBODIMENTS

Figure 1:
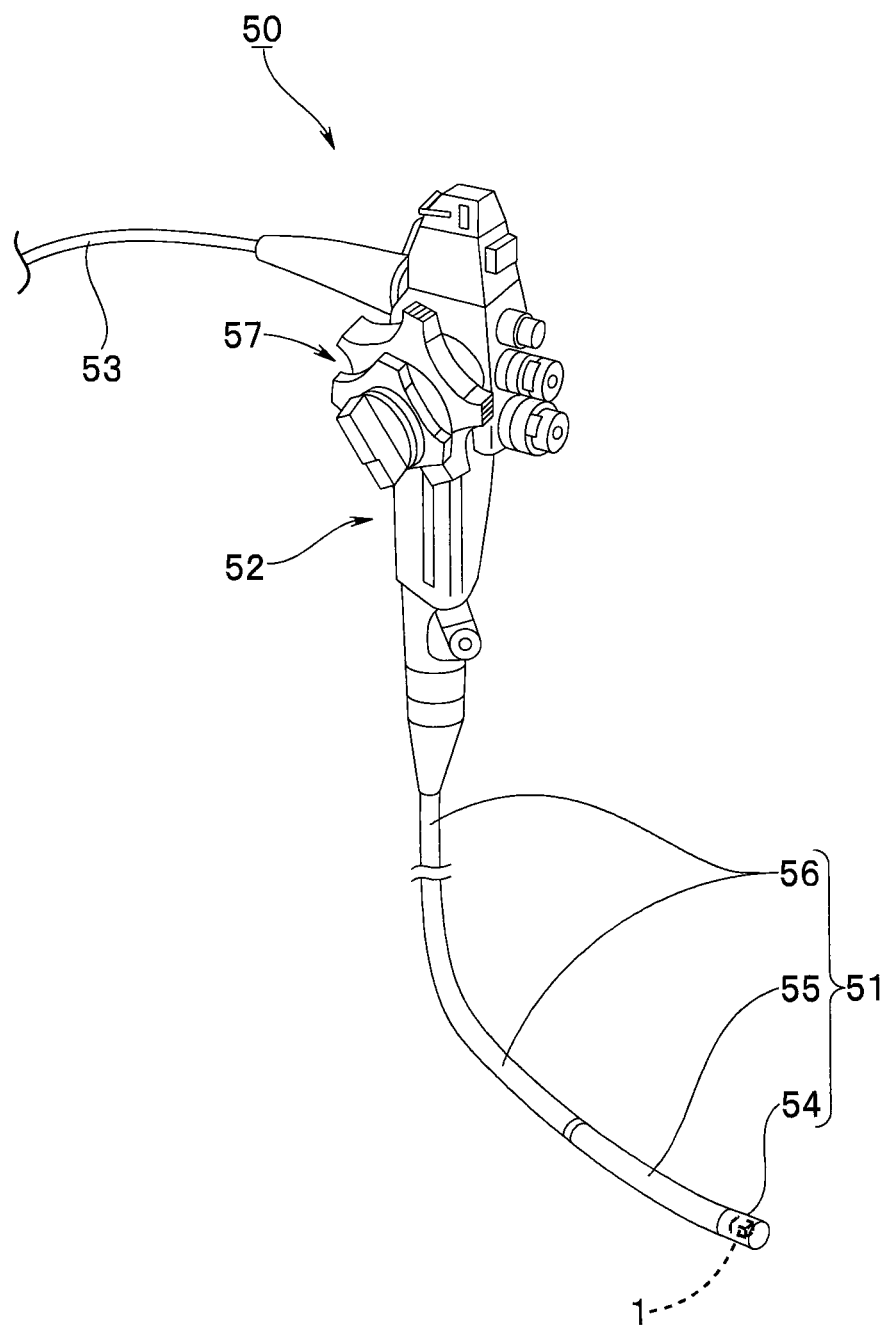
FIG. 1 is a diagram to explain an endoscope including an image pickup unit according to the present invention.

Some embodiments of the present invention are described below with reference to drawings.

Note that, in all drawings used in the following description, scale size is varied for each component in order to illustrate each component with a recognizable size in the drawings. The present invention is not limited to only the number of components, shapes of the respective components, a size ratio of the components, and relative positional relationship between the components illustrated in the drawings.

A first embodiment of an image pickup apparatus is described with reference to FIG. 1 to FIG. 3G.

As illustrated in FIG. 1, an endoscope 50 includes an insertion section 51, an operation section 52, and a universal cable 53 that is an electric cable. The insertion section 51 of the endoscope 50 includes a distal end portion 54, a bending portion 55, and a flexible tube portion 56 in order from a distal end.

An image pickup apparatus 1 described later is incorporated in the distal end portion 54 of the insertion section 51.

The operation section 52 is continuous to proximal end side of the flexible tube portion 56 that configures the insertion section 51. The operation section 52 includes a bending operation portion 57 that bends the bending portion 55 of the insertion section 51, and the like.

Figure 2:
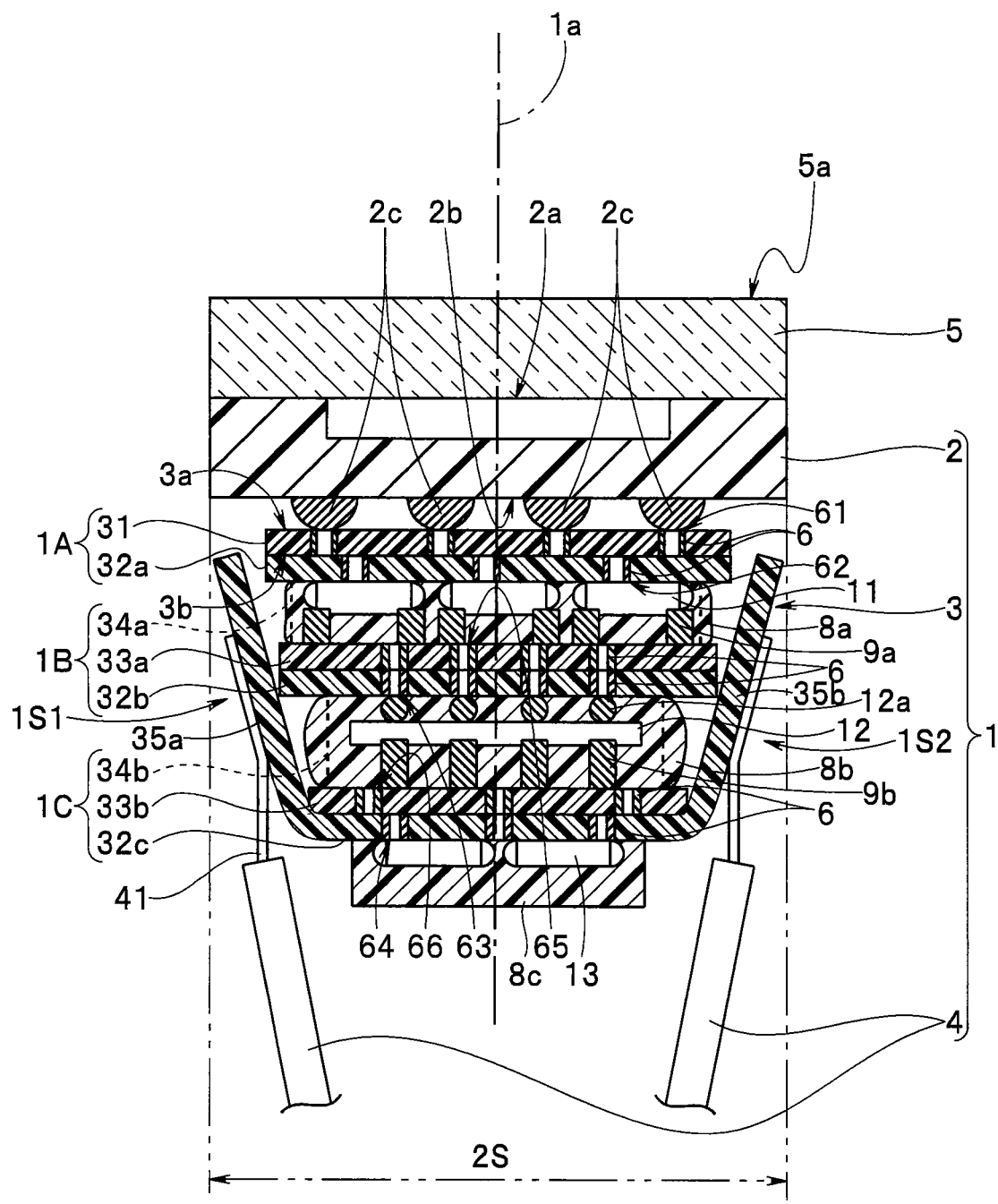
FIG. 2 is a cross-sectional diagram to explain a configuration of an image pickup apparatus according to a first embodiment.

As illustrated in FIG. 2, the image pickup apparatus 1 mainly includes a rectangular-parallelepiped solid-state image pickup device (hereinafter, referred to as an image pickup device) 2, a folded flexible substrate 3, and signal cables 4.

A reference numeral 1a denotes an image pickup apparatus longitudinal axis or an axis orthogonal to a light receiving surface 2a of the image pickup device 2. The signal cables 4 extend in a longitudinal direction along the image pickup apparatus longitudinal axis 1a.

The image pickup device 2 includes the light receiving surface 2a, and a cover glass 5 is fixed to the light receiving surface 2a. A front surface 5a of the cover glass 5 is a most distal end surface of the image pickup device 2. A plurality of device contacts 2c are arranged on a rear surface 2b that is opposite to the light receiving surface 2a of the image pickup device 2.

The front surface 5a of the cover glass 5 has the surface shape substantially the same as a surface shape of a surface of the cover glass 5 on side close to the light receiving surface 2a of the image pickup device 2. In other words, the surface shapes and areas of the respective surfaces of the cover glass 5 are set to be substantially the same as each other.

The flexible substrate 3 is a resin substrate and has predetermined flexibility. The resin substrate includes a base substance that is an insulation material such as polyimide and polyethylene terephthalate, and for example, a copper foil serving as a conductor foil.

Figure 3A:
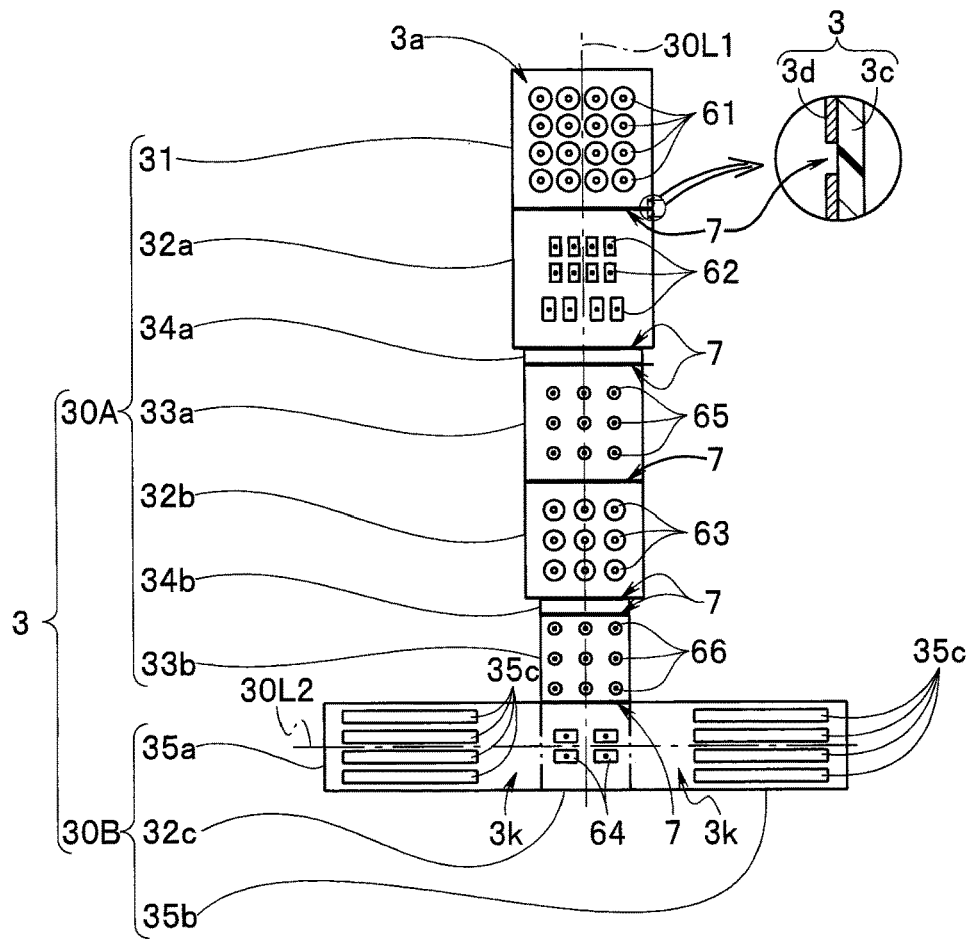
FIG. 3A is a diagram illustrating first surface side of an unfolded flexible substrate according to the first embodiment.

As illustrated in FIG. 3A, the flexible substrate 3 according to the present embodiment has a reversed T shape in an unfolded state. The flexible substrate 3 is sequentially folded as illustrated in FIG. 3D, and is entirely fitted within a projected area region 2S of the image pickup device 2 as illustrated in FIG. 2.

The flexible substrate 3 includes a plurality of functional regions. The functional regions include, for example, one image pickup device mounting region 31, three electronic component mounting regions 32a, 32b, and 32c, two wiring regions 33a and 33b, two folding margin regions 34a and 34b, and two cable mounting regions 35a and 35b.

In the present embodiment, the flexible substrate 3 includes a first strip portion 30A and a second strip portion 30B. A first longitudinal-direction centerline (hereinafter, abbreviated to first centerline) 30L1 of the first strip portion 30A and a second longitudinal-direction centerline (hereinafter, abbreviated to second centerline) 30L2 of the second strip portion 30B are orthogonal to each other.

The first strip portion 30A includes the image pickup device mounting region 31, the first electronic component mounting region 32a, the first folding margin region 34a, the first wiring region 33a, the second electronic component mounting region 32b, the second folding margin region 34b, and the second wiring region 33b that are disposed in a straight line along the first centerline 30L1.

The second strip portion 30B includes the first cable mounting region 35a, the third electronic component mounting region 32c, and the second cable mounting region 35b that are disposed in a straight line along the second centerline 30L2.

In the present embodiment, the flexible substrate 3 has a T shape in which an end surface of the first strip portion 30A on the second wiring region 33b side and a side surface including the third electronic component mounting region 32*c* of the second strip portion 30B are coupled to each other.

An unillustrated wiring pattern is provided on each of a first surface 3*a* and a second surface 3*b* of the image pickup device mounting region 31, the electronic component mounting regions 32*a*, 32*b*, and 32*c*, and the wiring regions 33*a* and 33*b*. The second surface 3*b* is an opposite surface of the first surface 3*a*.

In addition, a plurality of through conductors 6 are provided on predetermined positions of each of the image pickup device mounting region 31, the electronic component mounting regions 32*a*, 32*b*, and 32*c*, and the wiring regions 33*a* and 33*b*. Each of the through conductors 6 is a wiring that penetrates through the first surface 3*a* and the second surface 3*b* to electrically connect the first surface 3*a* side and the second surface 3*b* side.

The image pickup device mounting region 31 has a rectangular shape corresponding to the image pickup device 2 and is set to a predetermined surface shape.

As illustrated in FIG. 3A, the first surface 3*a* of the image pickup device mounting region 31 is an image pickup device mounting surface. A plurality of device connection parts 61 are arranged on the first surface 3*a*. The plurality of device connection parts 61 are provided correspondingly to the device contacts 2*c* of the image pickup device 2.

Figure 3B:
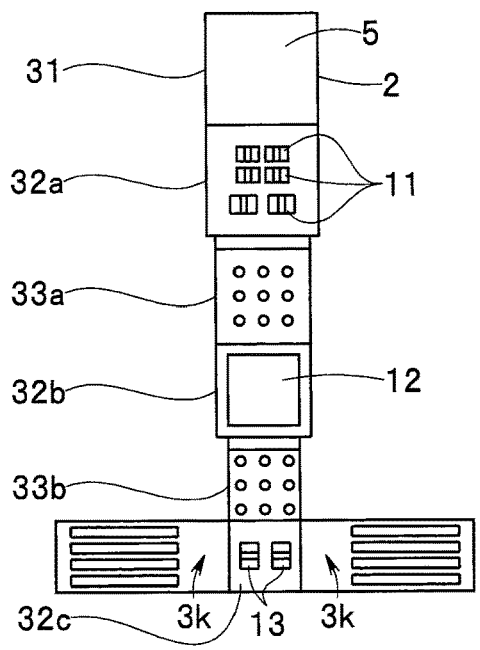
FIG. 3B is a diagram illustrating the first surface of the flexible substrate illustrated in FIG. 3A on which an image pickup device and electronic components are mounted.

As illustrated in FIG. 2 and FIG. 3B, the image pickup device 2 to which the cover glass 5 is integrally fixed is mounted on the first surface 3*a* of the image pickup device mounting region 31.

At least one electronic component is mounted on each of the electronic component mounting regions 32*a*, 32*b*, and 32*c*.

The electronic component is a passive component such as a capacitor and a resistor, or an active component performing signal processing, such as an IC. The electronic component performs processing of an electric signal outputted from the image pickup device 2, processing of driving power, and other processing.

As illustrated in FIG. 3A, the first electronic component mounting region 32*a* has the rectangular shape the same as the shape of the image pickup device mounting region 31. A surface shape of the first electronic component mounting region 32*a* is set to be substantially the same as the surface shape of the image pickup device mounting region 31.

The first surface 3*a* of the first electronic component mounting region 32*a* is a first electronic component mounting surface, and includes a plurality of first electronic component connection parts 62. The plurality of first electronic component connection parts 62 correspond to first electronic components 11. As illustrated in FIG. 2 and FIG. 3B, the first electronic components 11 are respectively mounted on the first electronic component connection parts 62.

As illustrated in FIG. 3A, the second electronic component mounting region 32*b* also has the rectangular shape the same as the shape of the image pickup device mounting region 31. A surface shape of the second electronic component mounting region 32*b* is previously set smaller than the surface shape of the first electronic component mounting region 32*a*. At this time, the fact that a surface shape of one surface is smaller than a surface shape of the other surface indicates that the one surface is smaller in length of each of at least paired opposing sides than the other surface.

The first surface 3*a* of the second electronic component mounting region 32*b* is a second electronic component mounting surface, and includes a plurality of second electronic component connection parts 63. The plurality of second electronic component connection parts 63 correspond to a second electronic component 12. As illustrated in FIG. 2 and FIG. 3D, the second electronic component 12 is mounted on the second electronic component connection parts 63 through, for example, connection members 12*a* serving as bump electrodes.

As illustrated in FIG. 3A, the third electronic component mounting region 32*c* also has the rectangular shape the same as the shape of the image pickup device mounting region 31. A surface shape of the third electronic component mounting region 32*c* is previously set smaller than the surface shape of the second electronic component mounting region 32*b*.

The first surface 3*a* of the third electronic component mounting region 32*c* is a third electronic component mounting surface, and includes a plurality of third electronic component connection parts 64. The plurality of third electronic component connection parts 64 correspond to third electronic components 13. As illustrated in FIG. 2 and FIG. 3B, the third electronic components 13 are respectively mounted on the third electronic component connection parts 64.

Figure 3C:
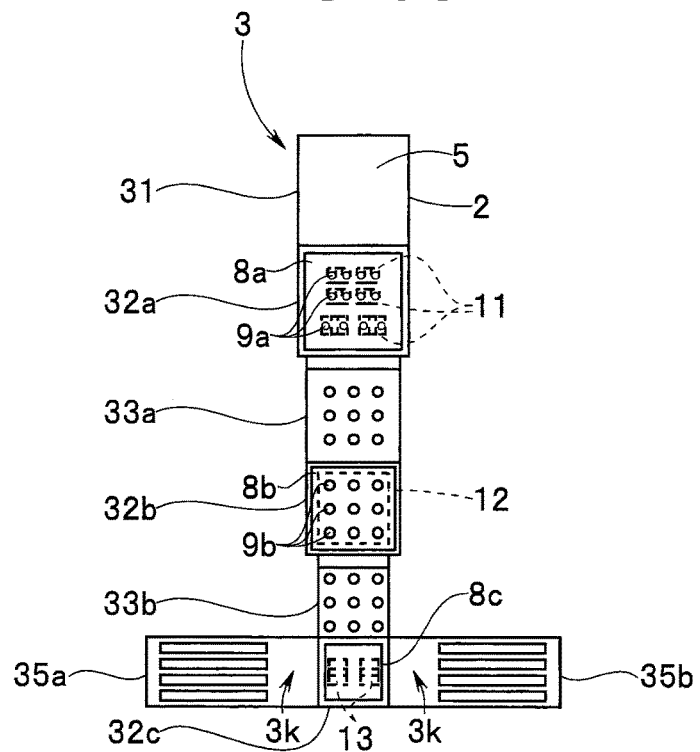
FIG. 3C is a diagram to explain a state in which the electronic components mounted on the first surface of the flexible substrate illustrated in FIG. 3B are sealed with sealing resins.
Figure 3D:
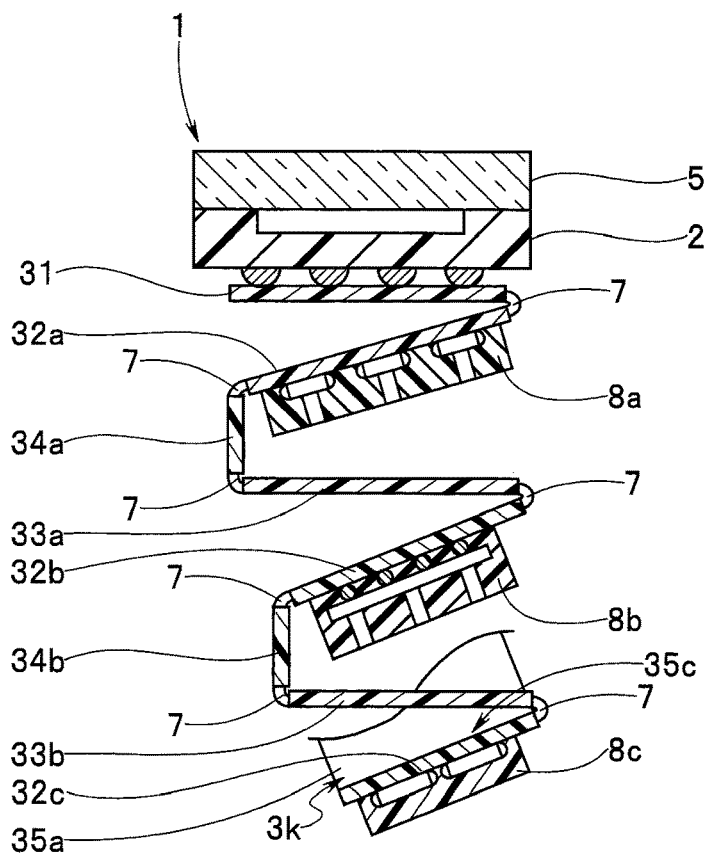
FIG. 3D is a cross-sectional diagram to explain folding of the flexible substrate illustrated in FIG. 3C.

Further, as illustrated in FIG. 3C and FIG. 3D, sealing resins 8*a*, 8*b*, and 8*c* that respectively seal and fix the electronic components 11, 12, and 13 mounted on the first surfaces 3*a* are provided on the flexible substrate 3 in the unfolded state.

The first sealing resin 8*a* seals first connection electrodes 9*a* and the first electronic components 11. The first connection electrodes 9*a* are columnar electrodes provided on the respective first electronic components 11 mounted on the first electronic component mounting region 32*a*.

The second sealing resin 8*b* seals second connection electrodes 9*b*, the second electronic component 12, and the connection members 12*a*. The second connection electrodes 9*b* are columnar electrodes provided on the second electronic component 12 mounted on the second electronic component mounting region 32*b*.

The third sealing resin 8*c* seals the third electronic components 13 mounted on the third electronic component mounting region 32*c*.

Surfaces of the above-described respective sealing resins 8*a*, 8*b*, and 8*c* are so molded as to be parallel to the first surfaces 3*a* of the respective electronic component mounting regions 32*a*, 32*b*, and 32*c*. In addition, the sealing resins 8*a*, 8*b*, and 8*c* are desirably formed through collective sealing by a printing method.

As illustrated in FIG. 3A and FIG. 3B, the first wiring region 33*a* also has the rectangular shape the same as the shape of the image pickup device mounting region 31. A surface shape of the first wiring region 33*a* is set to be substantially the same as the surface shape of the second electronic component mounting region 32*b*.

A plurality of predetermined through wirings 65 are provided on the first wiring region 33*a*. The plurality of through wirings 65 electrically connect a plurality of contact parts (not illustrated) on a surface of the first sealing resin 8*a* and a plurality of contact parts (not illustrated) of the second electronic component mounting region 32*b*, that are stacked.

The second wiring region 33*b* also has the rectangular shape the same as the shape of the image pickup device mounting region 31. A surface shape of the second wiring region 33*b* is set to be substantially the same as the surface shape of the third electronic component mounting region 32*c*.

A plurality of predetermined through wirings 66 are provided on the second wiring region 33*b*. The plurality of through wirings 66 electrically connect a plurality of contact parts (not illustrated) on a surface of the second sealing resin 8b and a plurality of contact parts (not illustrated) of the third electronic component mounting region 32c, that are stacked.

The first folding margin region 34a defines a distance between the first wiring region 33a and the first electronic component mounting region 32a in the image pickup apparatus longitudinal axis 1a direction. Therefore, the first folding margin region 34a has a previously-set length in the first centerline 30L1 direction in consideration of heights of the first electronic components 11 mounted on the first electronic component mounting region 32a and a height of the first sealing resin 8a, etc.

As a result, the first surface 3a of the first wiring region 33a is so foldable as to face the first surface 3a of the first electronic component mounting region 32a.

In contrast, the second folding margin region 34b defines a distance between the second wiring region 33b and the second electronic component mounting region 32b in the image pickup apparatus longitudinal axis 1a direction. Therefore, the second folding margin region 34b has a previously-set length in the first centerline 30L1 direction in consideration of heights of the second electronic component 12 mounted on the second electronic component mounting region 32b and a height of the second sealing resin 8b, etc.

As a result, the first surface 3a of the second wiring region 33b is so foldable as to face the first surface 3a of the second electronic component mounting region 32b.

Each of the cable mounting regions 35a and 35b has a previously-set length in the second centerline 30L2 direction. A plurality of signal line connection parts 35c are provided on the first surface 3a of each of the cable mounting regions 35a and 35b. Signal lines 41 in the signal cables 4 are respectively connected to the corresponding signal line connection parts 35c.

A reference numeral 3k denotes a sixth bending region or a sixth bending portion included in each of the cable mounting regions 35a and 35b. A wiring pattern (not illustrated) is provided on the first surface 3a of each of the cable mounting regions 35a and 35b.

A reference numeral 7 in FIG. 3A denotes a bending portion. The bending portion 7 corresponds to a folding line when adjacent regions are folded. As illustrated in an enlarged view of FIG. 3A, the bending portion 7 is a portion configured of only a base substance 3c that is obtained by removing a copper foil 3d from the base substance 3c configuring the flexible substrate 3 in a direction orthogonal to the first centerline 30L1.

The bending portion 7 having the configuration allows for folding with a bending radius that is smaller than a bending radius of the flexible substrate 3 on which the copper foil 3d is stacked.

As illustrated in FIG. 3A, in the present embodiment, the image pickup device mounting region 31 and the first electronic component mounting region 32a are segmented by the bending portion 7. The first electronic component mounting region 32a and the first folding margin region 34a are segmented by the bending portion 7. The first folding margin region 34a and the first wiring region 33a are segmented by the bending portion 7. The first wiring region 33a and the second electronic component mounting region 32b are segmented by the bending portion 7. The second electronic component mounting region 32b and the second folding margin region 34b are segmented by the bending portion 7. The second folding margin region 34b and the second wiring region 33b are segmented by the bending portion 7. The second wiring region 33b and the third electronic component mounting region 32c are segmented by the bending portion 7.

As illustrated in FIG. 3D, the image pickup device mounting region 31 and the first electronic component mounting region 32a are foldable through the bending portion 7 and are so folded as to bring the second surfaces 3b into close contact with each other. Further, in the folded state, the contacts provided on the image pickup device mounting region 31 and the contact parts provided on the first electronic component mounting region 32a are electrically connected and integrated to configure a first layer 1A as illustrated in FIG. 2.

As illustrated in FIG. 3D, the first electronic component mounting region 32a and the first wiring region 33a are foldable at a substantially right angle at the two bending portions 7 near the first folding margin region 34a, and are folded in a state where the first surface 3a of the first electronic component mounting region 32a and the first surface 3a of the first wiring region 33a face each other. Further, in the folded state, the plurality of contact parts on the surface of the first sealing resin 8a provided on the first electronic component mounting region 32a and the contact parts of the first wiring region 33a are electrically connected and integrated as illustrated in FIG. 2.

As a result, the first wiring region 33a is stacked on the first layer 1A with the first folding margin region 34a in between.

As illustrated in FIG. 3D, the first wiring region 33a and the second electronic component mounting region 32b are foldable through the bending portion 7 and are so folded as to bring the second surfaces 3b into close contact with each other. Further, in the folded state, the contact parts provided on the first wiring region 33a and the contact parts provided on the second electronic component mounting region 32b are electrically connected and integrated to configure a second layer 1B as illustrated in FIG. 2.

As a result, the second layer 1B is stacked on the first layer 1A with the first folding margin region 34a in between.

As illustrated in FIG. 3D, the second electronic component mounting region 32b and the second wiring region 33b are foldable at a substantially right angle at the two bending portions 7 near the second folding margin region 34b, and are folded in a state where the first surface 3a of the second electronic component mounting region 32b and the first surface 3a of the second wiring region 33b face each other. Further, in the folded state, the plurality of contact parts on the surface of the second sealing resin 8b provided on the second electronic component mounting region 32b and the contact parts of the second wiring region 33b are electrically connected and integrated as illustrated in FIG. 2.

As a result, the second wiring region 33b is stacked on the second layer 1B with the second folding margin region 34b in between.

As illustrated in FIG. 3D, the second wiring region 33b and the third electronic component mounting region 32c are foldable through the bending portion 7 and are so folded as to bring the second surfaces 3b into close contact with each other. Further, in the folded state, the contact parts provided on the second wiring region 33b and the contact parts provided on the third electronic component mounting region 32c are electrically connected and integrated to configure a third layer 1C as illustrated in FIG. 2.

As a result, the third layer 1C is stacked on the second layer 1B with the second folding margin region 34b in between.

In the above-described stacked state, the surface shape of the first electronic component mounting region 32a and the surface shape of the image pickup device mounting region 31 in the first layer 1A are set to be substantially the same as each other.

The surface shape of the second electronic component mounting region 32b in the second layer 1B is previously set smaller than the surface shape of the first electronic component mounting region 32a. The surface shape of the second electronic component mounting region 32b and the surface shape of the first wiring region 33a are substantially the same as each other.

The surface shape of the third electronic component mounting region 32c in the third layer 1C is previously set smaller than the surface shape of the second electronic component mounting region 32b. The surface shape of the third electronic component mounting region 32c and the surface shape of the second wiring region 33b are substantially the same as each other.

In other words, each of the sides forming the surface shape of each layer is decreased in length in a stepwise manner in order of the first layer 1A, the second layer 1B, and the third layer 1C.

Figure 3E:
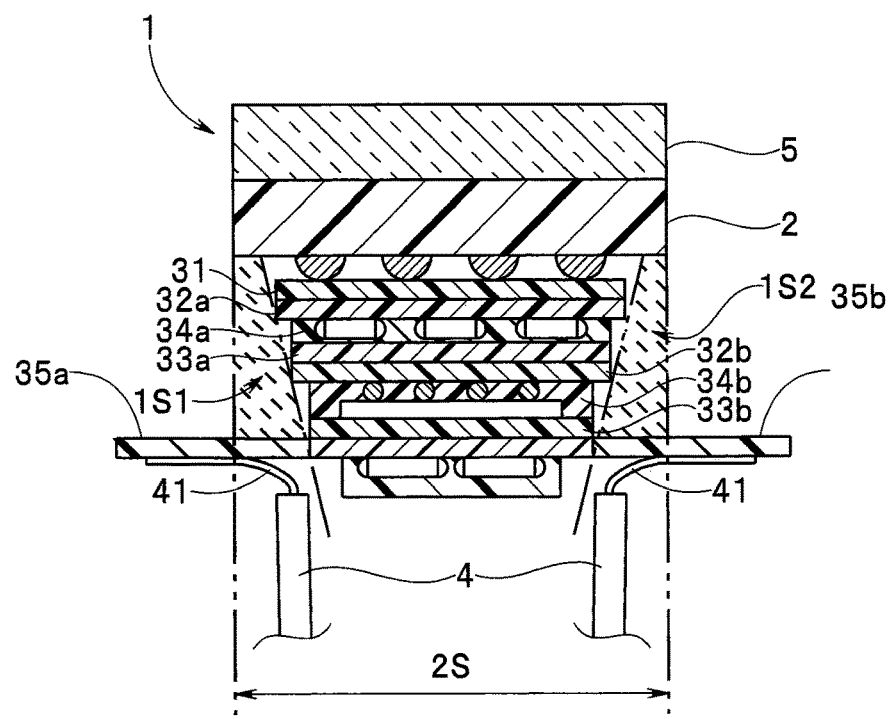
FIG. 3E is a cross-sectional diagram to explain spaces that appear when the flexible substrate is folded to be in a truncated square pyramid shape.

Accordingly, the first layer 1A, the second layer 1B, and the third layer 1C of the image pickup apparatus 1 that are stacked and integrated form a truncated square pyramid shape in which the front surface 5a of the cover glass 5 serves as a bottom surface and the third electronic component mounting region 32c serves as a top surface as illustrated in FIG. 2 and FIG. 3E.

As a result, spaces 1S1 and 1S2 in which the image pickup device mounting region 31, the first electronic component mounting region 32a, the first folding margin region 34a, the first wiring region 33a, the second electronic component mounting region 32b, the second folding margin region 34b, the second wiring region 33b, and the third electronic component mounting region 32c are not disposed appear within the projected area region 2S of the image pickup device 2 that is orthogonal to the image pickup apparatus longitudinal axis 1a.

The spaces 1S1 and 1S2 are cable mounting region installation spaces. As illustrated in FIG. 3D, the cable mounting regions 35a and 35b that are adjacent to the third electronic component mounting region 32c are folded at the sixth bending portion 3k toward the rear surface 2b of the image pickup device 2.

As a result, as illustrated in FIG. 2, the first cable mounting region 35a is disposed within the first space 1S1 while being close to one side part of the third layer 1C, one side part of the second layer 1B, and one side part of the first layer 1A. In contrast, the second cable mounting region 35b is disposed within the second space 1S2 while being close to the other side part of the third layer 1C that is an opposite surface of the one side part, the other side part of the second layer 1B, and the other side part of the first layer 1A.

As described above, according to the configuration of the present embodiment, the plurality of mounting regions 31, 32a, 32b, and 32c, the wiring regions 33a and 33b, and the folding margin regions 34a and 34b are provided on the flexible substrate 3 configuring the image pickup apparatus 1, these regions are disposed in a straight line to configure the strip portion 30A, and the bending portion 7 that is obtained by removing the copper foil 3d from the substrate 3 is provided in each gap between the regions of the strip portion 30A.

According to the configuration, the functional regions such as the mounting regions 31, 32a, 32b, and 32c, the wiring regions 33a and 33b, and the folding margin regions 34a and 34b are clearly segmented with the bending portion 7 in between.

Further, configuring the bending portion 7 by the base substance 3c makes it possible to fold the functional regions adjacent to each bending portion 7 at a right angle. This makes it possible to fold the functional regions while bring the surfaces into close contact with one another.

As a result, it is possible to stack the plurality of functional regions in the image pickup apparatus longitudinal axis 1a direction and to reduce the length of the image pickup apparatus 1 in the image pickup apparatus longitudinal axis 1a direction.

In addition, among the plurality of functional regions stacked on the rear surface 2b side of the image pickup device 2 in the image pickup apparatus longitudinal axis 1a direction, the first layer 1A having the largest surface shape is disposed near the rear surface of the image pickup device 2.

Further, the second layer 1B that has the surface shape smaller than the surface shape of the first layer 1A configures the lower layer of the first layer 1A, and the third layer 1C that has the surface shape smaller than the surface shape of the second layer 1B configures the lower layer of the second layer 1B.

In other words, the first layer 1A that has the largest surface shape is disposed near the rear surface of the image pickup device 2, and the surface shape is gradually decreased as a distance from the rear surface in the image pickup apparatus longitudinal axis 1a direction increases, thereby forming the stacked portion of the image pickup apparatus 1 in a truncated square pyramid shape.

Note that the shape of the stacked portion of the image pickup apparatus 1 is not limited to the truncated square pyramid shape, and the stacked portion of the image pickup apparatus 1 may have a truncated conical shape in which a head part of a circular cone is cut off at a plane parallel to a bottom surface, or other pyramid shape in which a head part of the pyramid is cut off.

As a result, the spaces 1S1 and 1S2 in which the functional regions are not disposed appear within the projected area region 2S of the image pickup device 2, and the first space 1S1 and the second space 1S2 serve as the spaces in which the cable mounting regions 35a and 35b are respectively disposed.

Therefore, it is possible to provide the image pickup apparatus 1 that achieves higher density mounting, by respectively fitting the cable mounting regions 35a and 35b of the T-shaped flexible substrate 3 within the spaces 1S1 and 1S2 without folding the cable mounting regions 35a and 35b to increase the length in the image pickup apparatus longitudinal axis 1a direction.

Figure 3F:
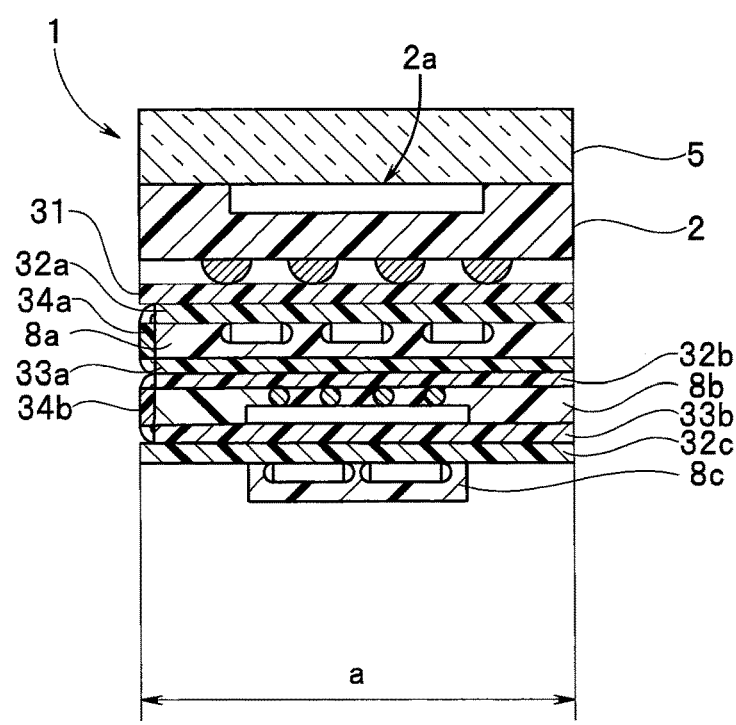
FIG. 3F is a cross-sectional diagram to explain a modification of the flexible substrate illustrated in FIG. 3C.

Note that the shape of the stacked portion of the image pickup apparatus 1 is not limited to the pyramid shape and the conical shape. Even if the shape of a part of the stacked portion without the cable mounting regions 35a and 35b has a straight shape as illustrated in FIG. 3F, it is possible to achieve function and effects similar to the function and effects described above.

Figure 3G:
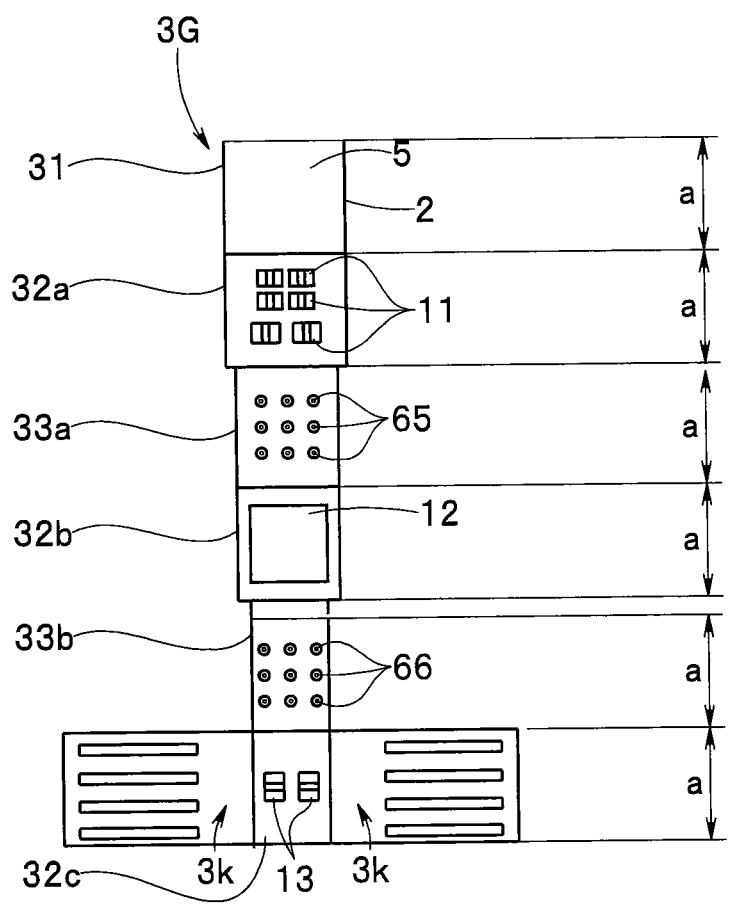
FIG. 3G is a diagram to explain a state in which the flexible substrate illustrated in FIG. 3F is unfolded.

A flexible substrate 3G has a configuration illustrated in FIG. 3G. In the flexible substrate 3G in the unfolded state, the length of each of paired sides in the longitudinal direction of each of the image pickup device mounting region 31, the first electronic component mounting region 32a, the first wiring region 33a, the second electronic component mounting region 32b, the second wiring region 33b, and the third electronic component mounting region 32c is set to a predetermined size a. The other configurations are similar to the configurations of the above-described flexible substrate 3.

The configuration makes it possible to reduce the surface shape of each of the regions 31, 32a, 33a, 32b, 33b, and 32c as a distance from the rear surface of the image pickup device 2 in the image pickup apparatus longitudinal axis 1a direction increases in a manner similar to the above description in the state where the regions 31, 32a, 33a, 32b, 33b, and 32c are folded, and to increase the area of each of the electronic component mounting regions 32a, 32b, and 32c on which the electronic components are mountable, as compared with the flexible substrate 3.

Further, in the flexible substrates 3 and 3G, a wiring pattern is provided on each of the first surfaces 3a and the second surfaces 3b of the respective functional regions, and the wirings of the wiring regions are configured of the through conductors 6 that penetrate and couple the first surfaces 3a and the second surfaces 3b. Further, the first connection electrodes 9a and the second connection electrodes 9b serving as the columnar electrodes are provided on the respective electronic components mounted on the electronic component mounting regions 32a and 32b.

Moreover, the contacts of the respective functional regions are electrically connected to one another in the folded state.

As a result, the wirings in the image pickup apparatus 1 that include the first layer 1A, the second layer 1B, and the third layer 1C are configured of the wiring patterns provided on the flat surface, the through conductors 6, the first connection electrodes 9a, the second connection electrodes 9b corresponding to the thickness of the flexible substrate 3, and the contact parts (not illustrated) on the respective surfaces. Therefore, it is possible to achieve high density mounting while achieving significant reduction of the wiring length in the image pickup apparatus 1.

Further, the image pickup apparatus 1 makes it possible to achieve noise reduction of a transmission signal through reduction of the wiring length.

Figure 4A:
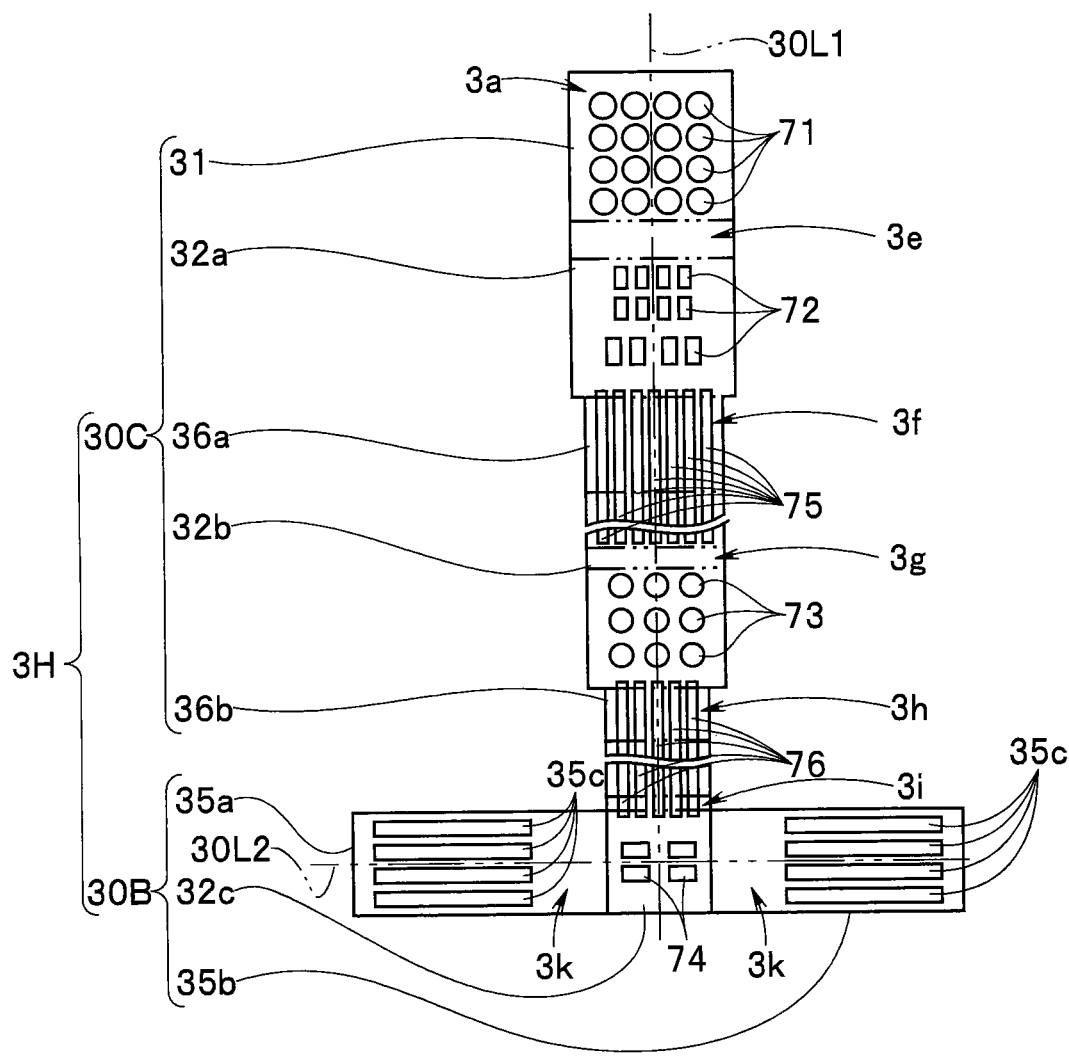
FIG. 4A is a diagram to explain a flexible substrate used in an image pickup apparatus according to a second embodiment.

A second embodiment of the present invention is described with reference to FIG. 4A to FIG. 4C.

In the present embodiment, a flexible substrate 3H of the image pickup apparatus 1 has predetermined flexibility. As illustrated in FIG. 4A, the flexible substrate 3H has a reversed T shape in an unfolded state, and includes a first strip portion 30C and the second strip portion 30B.

The first strip portion 30C according to the present embodiment includes the image pickup device mounting region 31, the first electronic component mounting region 32a, a first wiring region 36a, the second electronic component mounting region 32b, and a second wiring region 36b that are disposed in order from one end side in a straight line along the first centerline 30L1.

The second strip portion 30B includes the first cable mounting region 35a, the third electronic component mounting region 32c, and the second cable mounting region 35b that are disposed in order from one end side in a straight line along the second centerline 30L2.

Also in the present embodiment, the first centerline 30L1 and the second centerline 30L2 are orthogonal to each other as with the first embodiment.

The image pickup device mounting region 31 has a rectangular shape corresponding to the image pickup device 2, and is so set to a predetermined surface shape as to configure the first layer 1A. Note that the through conductor 6 is not provided in the image pickup device mounting region 31 according to the present embodiment.

The first surface 3a of the image pickup device mounting region 31 is an image pickup device mounting surface. A wiring pattern (not illustrated) and device connection parts 71 are provided on the first surface 3a. The plurality of device connection parts 71 are provided correspondingly to the device contacts 2c of the image pickup device 2. The image pickup device 2 to which the cover glass 5 is integrally fixed is mounted on the first surface 3a of the image pickup device mounting region 31.

At least one electronic component is mounted on each of the electronic component mounting regions 32a, 32b, and 32c. Note that the through conductor 6 is not provided in each of the electronic component mounting region 32a, 32b, and 32c according to the present embodiment.

The first electronic component mounting region 32a has the rectangular shape the same as the shape of the image pickup device mounting region 31. The surface shape of the first electronic component mounting region 32a is so set to be substantially the same as the surface shape of the image pickup device mounting region 31 as to configure the first layer 1A.

The first surface 3a of the first electronic component mounting region 32a is a first electronic component mounting surface, and a wiring pattern (not illustrated) and first electronic component connection parts 72 are provided on the first surface 3a of the first electronic component mounting region 32a. The first electronic component connection parts 72 correspond to the respective first electronic components 11.

The second electronic component mounting region 32b also has the rectangular shape the same as the shape of the image pickup device mounting region 31. The surface shape of the second electronic component mounting region 32b is so previously set smaller than the surface shape of the first electronic component mounting region 32a as to configure the second layer 1B.

The first surface 3a of the second electronic component mounting region 32b is a second electronic component mounting surface, and a wiring pattern (not illustrated) and second electronic component connection parts 73 are provided on the first surface 3a of the second electronic component mounting region 32b. The second electronic component connection parts 73 correspond to the second electronic component 12.

The third electronic component mounting region 32c also has the rectangular shape the same as the shape of the image pickup device mounting region 31. The surface shape of the third electronic component mounting region 32c is so previously set smaller than the surface shape of the second electronic component mounting region 32b as to configure the third layer 1C. The first surface 3a of the third electronic component mounting region 32c is a third electronic component mounting surface, and a wiring pattern (not illustrated) and third electronic component connection parts 74 are provided on the first surface 3a of the third electronic component mounting region 32c. The third electronic component connection parts 74 correspond to the respective third electronic components 13.

The first wiring region 36a also has the rectangular shape the same as the shape of the image pickup device mounting region 31. The surface shape of the first wiring region 36a is so configured to be substantially the same as the surface shape of the second electronic component mounting region 32b as to configure the second layer 1B. A plurality of wirings 75 in place of the plurality of through wirings 65 described above are provided in the first wiring region 36a.

The plurality of wirings 75 are provided at least on the first surface 3a of the first wiring region 36a, and electrically connect a plurality of contacts (not illustrated) provided in the first electronic component mounting region 32a and a plurality of contacts (not illustrated) provided on the second electronic component mounting region 32b. The first electronic component mounting region 32a and the second electronic component mounting region 32b are adjacent to both sides of the first wiring region 36a in the longitudinal direction.

The second wiring region 36b also has the rectangular shape the same as the shape of the image pickup device mounting region 31. The surface shape of the second wiring region 36b is so configured to be substantially the same as the surface shape of the third electronic component mounting region 32c as to configure the third layer 1C. A plurality of wirings 76 in place of the plurality of through wirings 66 described above are provided in the second wiring region 36b.

The plurality of wirings 76 are provided at least on the first surface 3a of the second wiring region 36b, and electrically connect a plurality of contacts (not illustrated) provided on the second electronic component mounting region 32b and a plurality of contacts (not illustrated) provided on the third electronic component mounting region 32c. The second electronic component mounting region 32b and the third electronic component mounting region 32c are adjacent to both sides of the second wiring region 36b in the longitudinal direction.

In other words, in the present embodiment, the through wirings 65 and 66 are not respectively provided in the wiring regions 36a and 36b. Further, in the present embodiment, the corresponding electronic components 11, 12, and 13 are respectively mounted on the electronic component mounting regions 32a, 32b, and 32c as well as are electrically connected to one another by the unillustrated wiring patterns and the wirings 75 and 76.

Furthermore, in the flexible substrate 3H of the present embodiment, a plurality of bending regions 3e, 3f, 3g, 3h, 3i, and 3k are provided as bending portions, in place of the bending portions 7 each configured of the base substance 3c described in the first embodiment.

A reference numeral 3e denotes a first bending region or a first bending portion. The first bending portion 3e is provided between the image pickup device mounting region 31 and the first electronic component mounting region 32a. The length of the first bending portion 3e in the image pickup apparatus longitudinal axis 1a direction is set to allow bending such that the second surface 3b of the image pickup device mounting region 31 and the second surface 3b of the first electronic component mounting region 32a are in close contact with each other.

A reference numeral 3f denotes a second bending region or a second bending portion. The second bending portion 3f is provided in the first wiring region 36a, and the length of the second bending portion 3f in the image pickup apparatus longitudinal axis 1a direction is set to include a folding margin considering the heights of the first electronic components 11 mounted on the first electronic component mounting region 32a, the height of the first sealing resin 8a, and the like.

Accordingly, when the second bending portion 3f is deformed in a predetermined bent state, the first surface 3a of the first wiring region 36a faces the first surface 3a of the first electronic component mounting region 32a.

A reference numeral 3g denotes a third bending region or a third bending portion. The third bending portion 3g is provided between the first wiring region 36a and the second electronic component mounting region 32b. The length of the third bending portion 3g in the image pickup apparatus longitudinal axis 1a direction is set to allow bending such that the second surface 3b of the first wiring region 36a and the second surface 3b of the second electronic component mounting region 32b are in close contact with each other.

A reference numeral 3h denotes a fourth bending region or a fourth bending portion. The fourth bending portion 3h is provided in the second wiring region 36b, and the length of the fourth bending portion 3h in the image pickup apparatus longitudinal axis 1a direction is set to include a folding margin considering the height of the second electronic component 12 mounted on the second electronic component mounting region 32b, the height of the second sealing resin 8b, and the like.

Accordingly, when the fourth bending portion 3h is deformed in a predetermined bent state, the first surface 3a of the second wiring region 36b faces the first surface 3a of the second electronic component mounting region 32b.

A reference numeral 3i denotes a fifth bending region or a fifth bending portion. The fifth bending portion 3i is provided in the second wiring region 36b. The length of the fifth bending portion 3i in the image pickup apparatus longitudinal axis 1a direction is set to allow bending such that the second surface 3b of the second wiring region 36b and the second surface 3b of the third electronic component mounting region 32c are in close contact with each other.

Other configurations of the flexible substrate 3H are similar to the configurations of the flexible substrate 3 of the first embodiment described above, and the same members are denoted by the same reference numerals and description of the members is omitted.

Figure 4B:
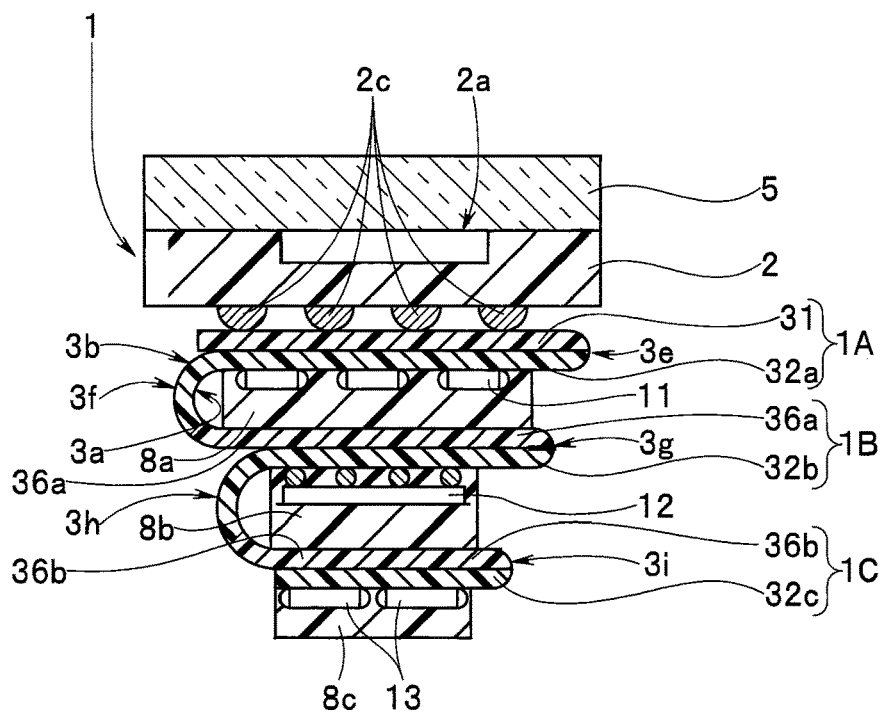
FIG. 4B is a cross-sectional diagram to explain a state in which the flexible substrate is folded.

As illustrated in FIG. 4B, the image pickup device mounting region 31 and the first electronic component mounting region 32a are folded at the first bending portion 3e at a predetermined curvature to bring the second surfaces 3b into close contact with each other. As a result, the image pickup device mounting region 31 and the first electronic component mounting region 32a are stacked to form the first layer 1A.

When the second bending portion 3f included in the first wiring region 36a is deformed in a predetermined bent state, the first wiring region 36a is so folded as to face the first electronic component mounting region 32a.

Further, the first wiring region 36a and the second electronic component mounting region 32b are folded at the third bending portion 3g at a predetermined curvature to bring the second surfaces 3b into close contact with each other. As a result, the first wiring region 36a and the second electronic component mounting region 32b are stacked to form the second layer 1B.

When the fourth bending portion 3h included in the second wiring region 36b is deformed in a predetermined bent state, the second wiring region 36b is so folded as to face the second electronic component mounting region 32b.

Further, the second wiring region 36b and the third electronic component mounting region 32c are folded at the fifth bending portion 3i included in the second wiring region 36b, at a predetermined curvature to bring the second surfaces 3b into close contact with each other. As a result, the second wiring region 36b and the third electronic component mounting region 32c are stacked to form the third layer 1C.

In the above-described stacked state, the surface shape of the first electronic component mounting region 32a is set to be substantially the same as the surface shape of the image pickup device mounting region 31. In contrast, the surface shape of the second electronic component mounting region 32b is previously set smaller than the surface shape of the first electronic component mounting region 32a, and the surface shape of the second electronic component mounting region 32b and the surface shape of the first wiring region 36a are set to be substantially the same as each other. Further, the surface shape of the third electronic component mounting region 32c is previously set smaller than the surface shape of the second electronic component mounting region 32b, and the surface shape of the third electronic component mounting region 32c and the surface shape of the second wiring region 36b are set to be substantially the same as each other.

Figure 4C:
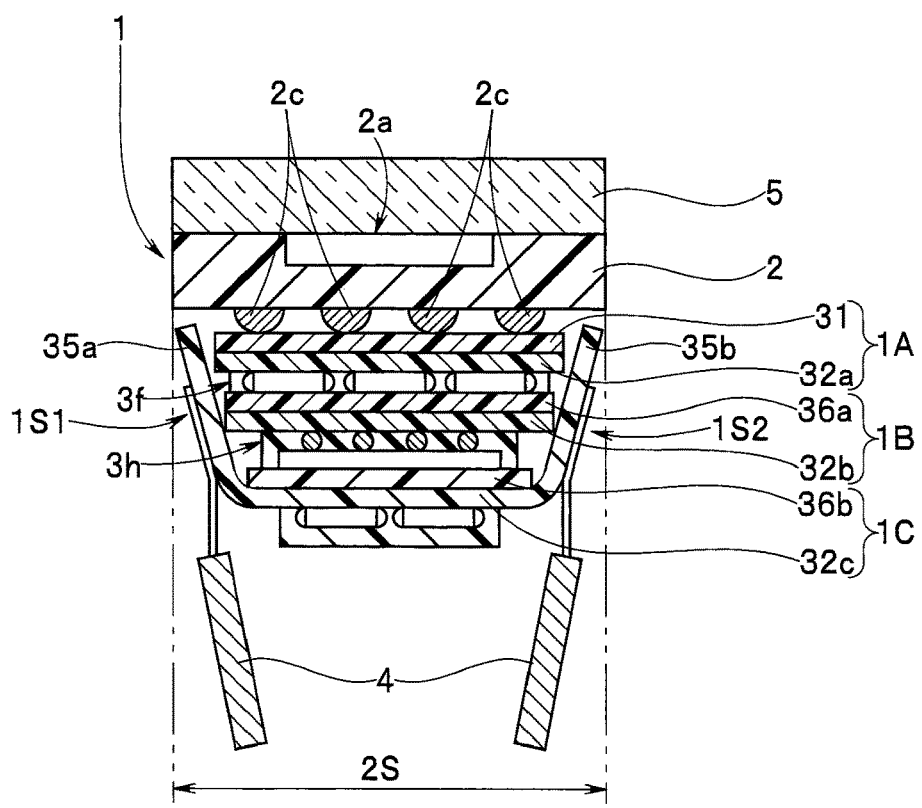
FIG. 4C is a cross-sectional diagram to explain the image pickup apparatus according to the second embodiment.

As a result, the image pickup apparatus 1 including the first layer 1A, the second layer 1B, and the third layer 1C that are stacked has a truncated square pyramid shape in which the front surface 5a of the cover glass 5 serves as the bottom surface and the third electronic component mounting region 32c serves as the top surface, as illustrated in FIG. 4C.

As a result, the spaces 1S1 and 1S2 in which the image pickup device mounting region 31, the first electronic component mounting region 32a, the first wiring region 36a, the second electronic component mounting region 32b, the second wiring region 36b, and the third electronic component mounting region 32c are not disposed appear within the projected area region 2S of the image pickup device 2.

The cable mounting regions 35a and 35b that are adjacent to the third electronic component mounting region 32c are bent at the respective bending regions 3k, and are laid down toward the rear surface 2b of the image pickup device 2.

As a result, as with the above-described embodiment, the first cable mounting region 35a is disposed within the first space 1S1 while being close to one side part of the third layer 1C, one side part of the second layer 1B, and one side part of the first layer 1A. In contrast, the second cable mounting region 35b is disposed within the second space 1S2 while being close to the other side part of the third layer 1C that is an opposite surface of the one side part, the other side part of the second layer 1B, and the other side part of the first layer 1A.

As described above, according to the configuration of the present embodiment, the plurality of mounting regions 31, 32a, 32b, and 32c and the wiring regions 36a and 36b are disposed in a straight line on the flexible substrate 3 configuring the image pickup apparatus 1, thereby configuring the strip portion 30C. Further, each of the bending portions 3e, 3f, 3g, 3h, 3i, and 3k each including the folding margin is provided, for example, in a corresponding gap between the mounting regions, or within the corresponding wiring region.

According to the configuration, each of the bending portions 3e, 3f, 3g, 3h, 3i, and 3k is deformed in the predetermined bent state. This makes it possible to configure the first layer 1A, the second layer 1B, and the third layer 1C in a truncated square pyramid shape while eliminating wiring breakage, thereby realizing the image pickup apparatus 1 that achieves function and effects similar to the function and effects of the above-described embodiment.

In addition, in the present embodiment, a plane wiring is provided in the bending portions 3e to 3i in the unfolded state, which electrically connect the electronic components to the wiring patterns. Accordingly, in the process of bending the flexible substrate 3 to provide the respective layers 1A, 1B, and 1C, it is possible to eliminate a work of electrically connecting the contacts to one another.

Figure 5A:
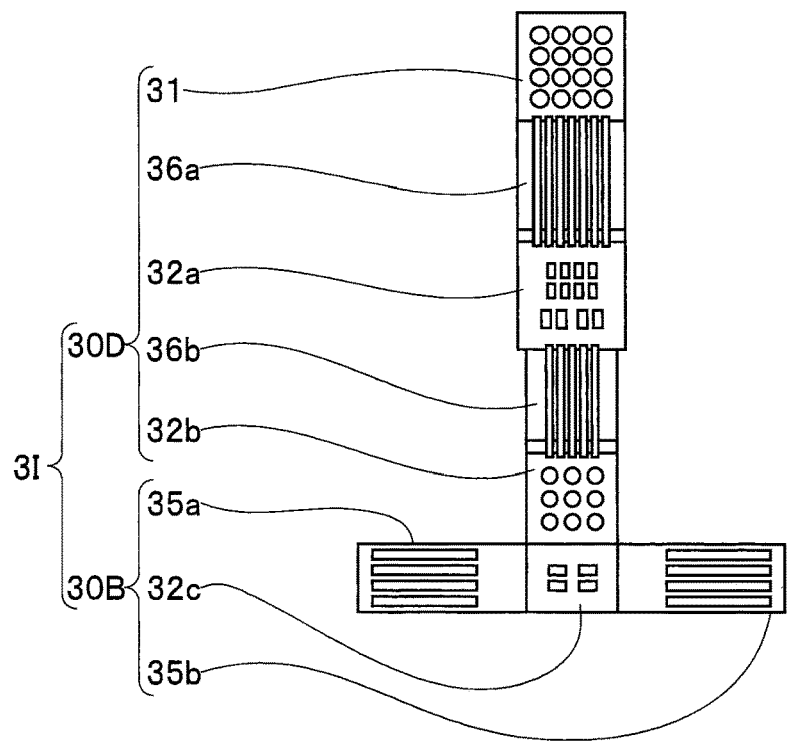
FIG. 5A is a diagram to explain a flexible substrate according to a modification of the image pickup apparatus of the second embodiment.

Note that, even when a flexible substrate 3I is configured of a first strip portion 30D and the second strip portion 30B as illustrated in FIG. 5A, it is possible to achieve similar function and effects.

In this configuration, the first strip portion 30D includes the image pickup device mounting region 31, the first wiring region 36a, the first electronic component mounting region 32a, the second wiring region 36b, and the second electronic component mounting region 32b that are disposed in a straight line in order from one end side.

Figure 5B:
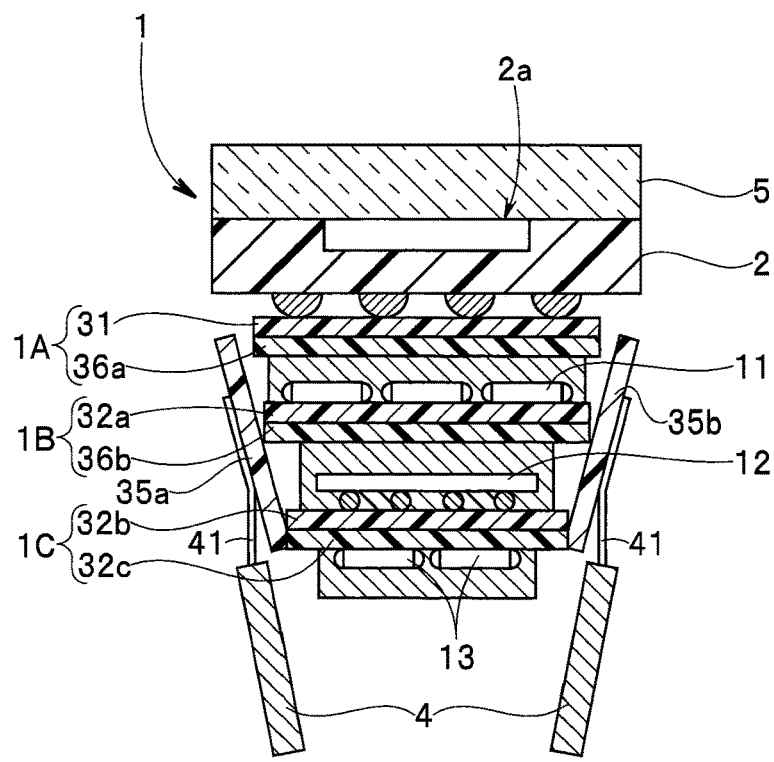
FIG. 5B is a cross-sectional diagram to explain the image pickup apparatus according to the modification.

Further, in the above-described configuration, the respective regions 31, 36a, 32a, 36b, 32b, and 32c are folded in a manner as illustrated in FIG. 5B, to configure the image pickup apparatus 1.

In the present embodiment, as illustrated in FIG. 5B, an installation direction of the first electronic components 11 mounted on the first electronic component mounting region 32a and an installation surface of the second electronic component 12 mounted on the second electronic component mounting region 32b are different from those in the second embodiment.

Further, in the present embodiment, the first layer 1A is configured of the image pickup device mounting region 31 and the first wiring region 36a, the second layer 1B is configured of the first electronic component mounting region 32a and the second wiring region 36b, and the third layer 1C is configured of the second electronic component mounting region 32b and the third electronic component mounting region 32c.

Accordingly, the surface shape of the first wiring region 36a and the surface shape of the image pickup device mounting region 31 in the first layer 1A are set to be substantially the same as each other. The surface shape of the first electronic component mounting region 32a in the second layer 1B is previously set smaller than the surface shape of the image pickup device mounting region 31, and the surface shape of the first electronic component mounting region 32a and the surface shape of the second wiring region 36b are set to be substantially the same as each other. The surface shape of the second electronic component mounting region 32b in the third layer 1C is previously set smaller than the surface shape of the first electronic component mounting region 32a, and the surface shape of the second electronic component mounting region 32b and the surface shape of the third electronic component mounting region 32c are set to be substantially the same as each other.

Other configurations are substantially similar to the configurations of the second embodiment described above, and the same members are denoted by the same reference numerals and description of the members is omitted.

Further, in the first embodiment, the second embodiment, and the like described above, the flexible substrates 3, 3G, 3H, and 3I each have a reversed T shape. The shape of the flexible substrate 3, however, is not limited to the reversed T shape, and may has an appropriately-set shape such as a T shape illustrated in FIG. 6A, a cross shape illustrated in FIG. 6B, and a strip shape illustrated in FIG. 6C.

Figure 6A:
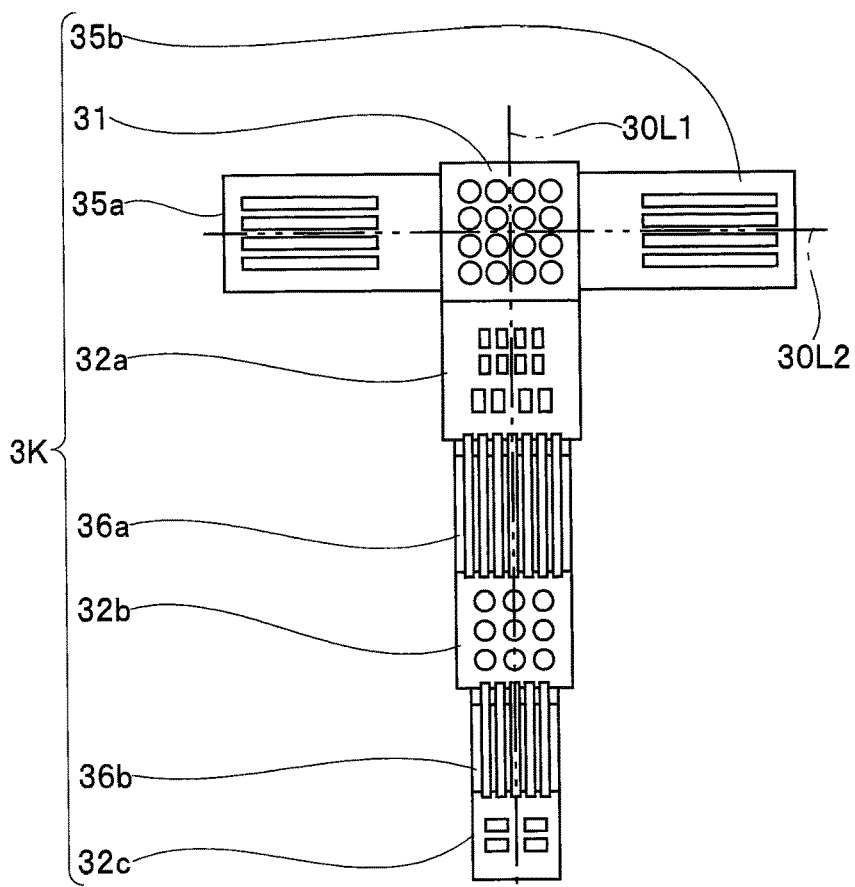
FIG. 6A is a diagram to explain another configuration of the flexible substrate.

In a flexible substrate 3K in FIG. 6A, the cable connection regions 35a and 35b are adjacent to the image pickup device mounting region 31. The other configurations are similar to the configurations of the above-described embodiments, and the same members are denoted by the same reference numerals and description of the members is omitted.

Figure 6B:
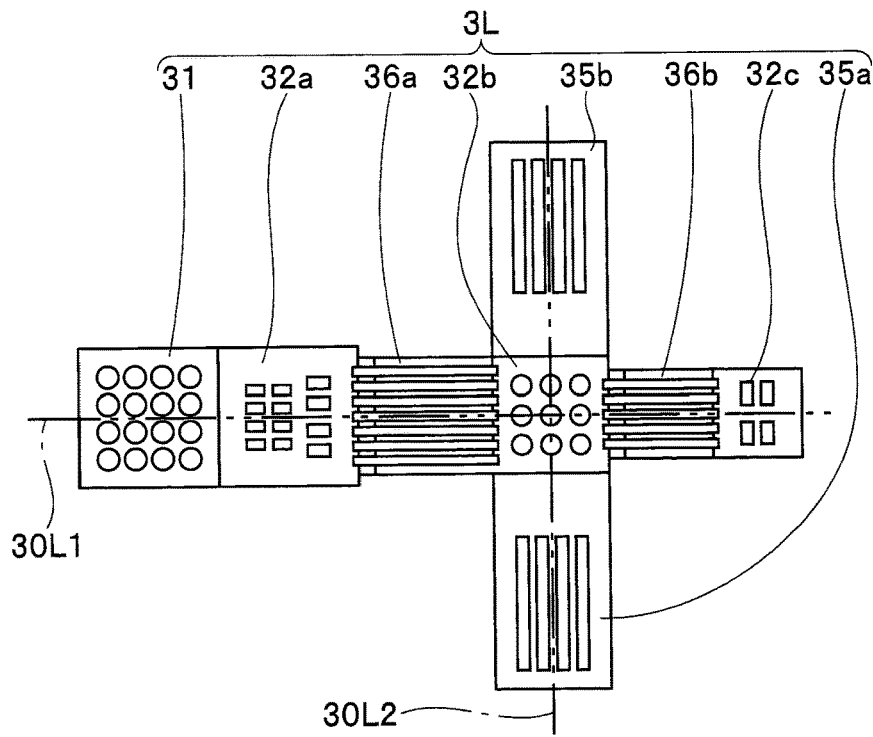
FIG. 6B is a diagram to explain still another configuration of the flexible substrate.

Further, in a flexible substrate 3L in FIG. 6B, the cable connection regions 35a and 35b are adjacent to the second electronic component mounting region 32b. The other configurations are similar to the configurations of the above-described embodiments, and the same members are denoted by the same reference numerals and description of the members is omitted.

Figure 6C:
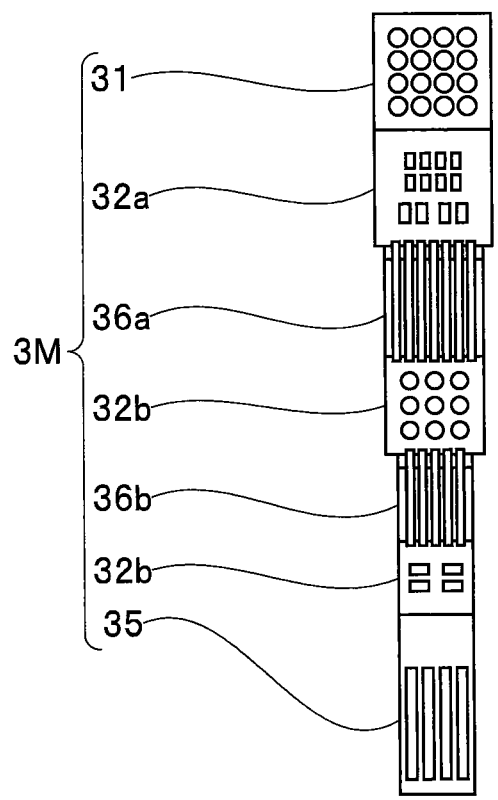
FIG. 6C is a diagram to explain still another configuration of the flexible substrate.

Moreover, when only one cable connection region 35 is provided as illustrated in FIG. 6C, a flexible substrate 3M has a configuration including only the first strip portion.

Note that the respective numbers of the electronic component mounting regions, the wiring regions, the folding margin regions, the cable mounting regions, and the layers provided in the flexible substrate described above are not limited to the respective numbers described in the above-described embodiments, and the number is appropriately increased or decreased as necessary.

Note that the present invention is not limited to only the above-described embodiments, and is variously modified and implemented without departing from the scope of the invention.

What is claimed is:

1. An image pickup apparatus, comprising:
   one solid-state image pickup device;
   a plurality of electronic components;
   at least one signal cable; and
   a flexible substrate that includes a first surface and a second surface, the flexible substrate having a predetermined flexibility and is formed in a predetermined shape in an unfolded state, the second surface being an opposite surface of the first surface, the flexible substrate including a plurality of functional regions that are separated from each other by one or more bending portions, the plurality of functional regions comprise:
   one image pickup device mounting region on which the solid-state image pickup device is mounted, the image pickup device mounting region having a predetermined rectangular surface shape,
   at least two electronic component mounting regions on which any of the electronic components is mounted, the electronic component mounting regions being folded at the bending portions to be disposed in parallel to the image pickup device mounting region, when folded, each of the two electronic component mounting regions being fitted within a projected area of the image pickup device mounting region,
   at least one wiring region provided between the at least two electronic component mounting regions adjacent to each other, the at least one wiring region including a wiring that electrically connects at least the electronic components of the at least two electronic component mounting regions, the at least one wiring region being folded to cause the at least two electronic component mounting regions to be parallel to the image pickup device mounting region, the at least one wiring region being fitted within the projected area of the image pickup device mounting region, and
   at least one cable mounting region connected to the signal cable, the at least one cable mounting region, together with the signal cable, are fitted within a space in which the electronic component mounting region and the wiring region are not disposed and within the projected area of the image pickup device mounting region,
   wherein, when folded into a stacked shape, the image pickup device mounting region has a largest surface shape among the plurality of stacked functional regions, and the plurality of stacked functional regions decrease in length at least between paired opposing sides of each surface shape, in a stepwise manner as a distance from the image pickup device mounting region increases, and
   the at least one cable mounting region is folded toward a rear surface of the image pickup device mounting region and, when folded, is fitted within the projected area of the image pickup device mounting region.

2. The image pickup apparatus according to claim 1, wherein at least a portion of the at least one wiring region is the bending portion.

3. The image pickup apparatus according to claim 1, wherein
   the image pickup device mounting region, the at least two electronic component mounting regions, and the at least one wiring region are disposed in series in a longitudinal direction of the flexible substrate in a state where the flexible substrate is unfolded,
   in the unfolded state, the image pickup device mounting region is disposed at one end,
   the at least one cable mounting region is connected to a first electronic component mounting region of the at least two electronic component mounting regions that is disposed furthest from the image pickup device mounting region, and
   the at least one cable mounting region is disposed adjacent to the first electronic component mounting region to extend from the first electronic component mounting region in a direction orthogonal to the longitudinal direction.

4. The image pickup apparatus according to claim 1, wherein the solid-state image pickup device and the at least two electronic components are mounted on a first surface of the flexible substrate in a state where the flexible substrate is unfolded.

5. The image pickup apparatus according to claim 1, wherein the at least one cable mounting region includes a signal line connection part that connects the signal cable to the at least one cable mounting region, the signal line connection part being disposed on a same surface as a surface on which the solid-state image pickup device and the at least two electronic components are mounted, in a state where the flexible substrate is unfolded.

6. The image pickup apparatus according to claim 1, wherein the at least one wiring region electrically connects two functional regions of the plurality of functional regions that are continuous to the at least one wiring region, through a wiring pattern provided on a surface of the flexible substrate.

7. The image pickup apparatus according to claim 1, wherein the at least one wiring region includes a through conductor that penetrates through and electrically connects the first surface and the second surface, the through conductor electrically connecting two functional regions of the plurality of functional regions that are continuous to the at least one wiring region.

8. The image pickup apparatus according to claim 7, wherein the flexible substrate comprising a base substance and a conductor foil, at least a part of the bending portions is formed of only the base substance of the flexible substrate with the conductor foil being removed in a direction orthogonal to a longitudinal direction of the flexible substrate in the unfolded state.

9. The image pickup apparatus according to claim 1, wherein, in a folded state of the substrate, a space is formed between an outer extent of the projected area of the image pickup device mounting region and at least a side surface of the at least two electronic component mounting regions, the at least one cable mounting region, when folded, being disposed within the space.

10. An endoscope comprising:
    an insertion section having a distal end configured to be inserted into a living body; and
    the image pickup apparatus according to claim 1 disposed in the distal end.

11. An image pickup apparatus, comprising:
    one solid-state image pickup device;
    a plurality of electronic components;
    at least one signal cable; and
    a flexible substrate that includes a first surface and a second surface, the flexible substrate having a predetermined flexibility and is formed in a predetermined shape in an unfolded state, the second surface being an opposite surface of the first surface, the flexible substrate including a plurality of functional regions that are separated from each other by one or more bending portions, the plurality of functional regions comprise:
        one image pickup device mounting region on which the solid-state image pickup device is mounted, the image pickup device mounting region having a predetermined rectangular surface shape,
        at least two electronic component mounting regions on which any of the electronic components is mounted, the electronic component mounting regions being folded at the bending portions to be disposed in parallel to the image pickup device mounting region, when folded, each of the two electronic component mounting regions being fitted within a projected area of the image pickup device mounting region,
        at least one wiring region provided between the at least two electronic component mounting regions adjacent to each other, the at least one wiring region including a wiring that electrically connects at least the electronic components of the at least two electronic component mounting regions, the at least one wiring region being folded to cause the at least two electronic component mounting regions to be parallel to the image pickup device mounting region, the at least one wiring region being fitted within the projected area of the image pickup device mounting region, and
    wherein, when folded into a stacked shape, the image pickup device mounting region has a largest surface shape among the plurality of stacked functional regions, and the plurality of stacked functional regions decrease in length at least between paired opposing sides, in a stepwise manner as a distance from the image pickup device mounting region increases, and
    the at least one wiring region includes a through conductor that penetrates through and electrically connects the first surface and the second surface, the through conductor electrically connecting two functional regions of the plurality of functional regions that are continuous to the at least one wiring region.

12. The image pickup apparatus according to claim 11, wherein the flexible substrate comprising a base substance and a conductor foil, at least a part of the bending portions is formed of only the base substance of the flexible substrate with the conductor foil being removed in a direction orthogonal to a longitudinal direction of the flexible substrate in the unfolded state.

\* \* \* \* \*